US012357697B2

(12) United States Patent
Tabuteau

(10) Patent No.: US 12,357,697 B2
(45) Date of Patent: *Jul. 15, 2025

(54) PHARMACEUTICAL COMPOSITIONS COMPRISING BUPROPION AND CYSTEINE

(71) Applicant: AXSOME THERAPEUTICS, INC., New York, NY (US)

(72) Inventor: Herriot Tabuteau, New York, NY (US)

(73) Assignee: AXSOME THERAPEUTICS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/921,291

(22) Filed: Oct. 21, 2024

(65) Prior Publication Data

US 2025/0041426 A1  Feb. 6, 2025

Related U.S. Application Data

(63) Continuation of application No. 18/169,402, filed on Feb. 15, 2023, now Pat. No. 12,156,914.

(60) Provisional application No. 63/370,777, filed on Aug. 8, 2022, provisional application No. 63/370,554, filed on Aug. 5, 2022, provisional application No. 63/357,318, filed on Jun. 30, 2022.

(51) Int. Cl.
| | | |
|---|---|---|
| *A61K 9/16* | (2006.01) | |
| *A61K 9/20* | (2006.01) | |
| *A61K 9/24* | (2006.01) | |
| *A61K 31/485* | (2006.01) | |
| *A61K 47/54* | (2017.01) | |

(52) U.S. Cl.
CPC .......... *A61K 47/542* (2017.08); *A61K 9/2009* (2013.01); *A61K 9/2013* (2013.01); *A61K 9/2054* (2013.01); *A61K 9/209* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 5,358,970 A * | 10/1994 | Ruff | A61K 47/183 514/769 |
| 5,731,000 A | 3/1998 | Ruff et al. | |
| 5,763,493 A | 6/1998 | Ruff et al. | |
| 6,306,436 B1 | 10/2001 | Chungi et al. | |
| 6,780,871 B2 | 8/2004 | Glick et al. | |
| 8,088,786 B2 | 6/2012 | McKinney et al. | |
| 8,569,328 B1 | 10/2013 | Tabuteau | |
| 9,168,234 B2 | 10/2015 | Tabuteau | |
| 9,198,905 B2 | 12/2015 | Tabuteau | |
| 9,205,083 B2 | 12/2015 | Tabuteau | |
| 9,238,032 B2 | 1/2016 | Tabuteau | |
| 9,278,095 B2 | 3/2016 | Tabuteau | |
| 9,314,462 B2 | 4/2016 | Tabuteau | |
| 9,364,458 B2 * | 6/2016 | Huang | A61K 9/2054 |
| 9,370,513 B2 | 6/2016 | Tabuteau | |
| 9,375,429 B2 | 6/2016 | Tabuteau | |
| 9,402,843 B2 | 8/2016 | Tabuteau | |
| 9,402,844 B2 | 8/2016 | Tabuteau | |
| 9,408,815 B2 | 8/2016 | Tabuteau | |
| 9,421,176 B1 | 8/2016 | Tabuteau | |
| 9,457,023 B1 | 10/2016 | Tabuteau | |
| 9,457,025 B2 | 10/2016 | Tabuteau | |
| 9,474,731 B1 | 10/2016 | Tabuteau | |
| 9,486,450 B2 | 11/2016 | Tabuteau | |
| 9,700,528 B2 | 7/2017 | Tabuteau | |
| 9,700,553 B2 | 7/2017 | Tabuteau | |
| 9,707,191 B2 | 7/2017 | Tabuteau | |
| 9,763,932 B2 | 9/2017 | Tabuteau | |
| 9,861,595 B2 | 1/2018 | Tabuteau | |
| 9,867,819 B2 | 1/2018 | Tabuteau | |
| 9,968,568 B2 | 5/2018 | Tabuteau | |
| 10,058,518 B2 | 8/2018 | Tabuteau | |
| 10,064,857 B2 | 9/2018 | Tabuteau | |
| 10,080,727 B2 | 9/2018 | Tabuteau | |
| 10,092,560 B2 | 10/2018 | Tabuteau | |
| 10,092,561 B2 | 10/2018 | Tabuteau | |
| 10,105,327 B2 | 10/2018 | Tabuteau | |
| 10,105,361 B2 | 10/2018 | Tabuteau | |
| 10,251,879 B2 | 4/2019 | Tabuteau | |
| 10,463,634 B2 | 11/2019 | Tabuteau | |
| 10,512,643 B2 | 12/2019 | Tabuteau | |
| 10,548,857 B2 | 2/2020 | Tabuteau | |

(Continued)

FOREIGN PATENT DOCUMENTS

| | | | |
|---|---|---|---|
| BR | 102016010170 A2 | 11/2017 | |
| EP | 4183391 A1 | 5/2023 | |

(Continued)

OTHER PUBLICATIONS

Spravato (esketamine), Highlights of Prescribing Information, revised Jul. 2020.
Nuedexta (dextromethorphan hydrobromide and quinidine sulfate), Highlights of Prescribing Information, revised Dec. 2022.
Aplenzin (bupropion hydrobromide), Highlights of Prescribing Information, revised Mar. 2022.
Tod et al., Quantitative Prediction of Cytochrome P450 (Cyp) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.

(Continued)

*Primary Examiner* — Susan T Tran
(74) *Attorney, Agent, or Firm* — Procopio, Cory, Hargreaves & Savitch LLP; Brent Johnson; Yuefen Zhou

(57) ABSTRACT

This disclosure relates to pharmaceutical compositions comprising bupropion and cysteine, and pharmaceutical dosage forms comprising bupropion and cysteine. The disclosure also relates to molecular complexes of bupropion and cysteine. These compositions and dosage forms may have improved stability of bupropion.

17 Claims, No Drawings

(56) References Cited

U.S. PATENT DOCUMENTS

| | | |
|---|---|---|
| 10,596,167 B2 | 3/2020 | Tabuteau |
| 10,688,066 B2 | 6/2020 | Tabuteau |
| 10,695,304 B2 | 6/2020 | Tabuteau |
| 10,772,850 B2 | 9/2020 | Tabuteau |
| 10,780,064 B2 | 9/2020 | Tabuteau |
| 10,780,066 B2 | 9/2020 | Tabuteau |
| 10,786,469 B2 | 9/2020 | Tabuteau |
| 10,786,496 B2 | 9/2020 | Tabuteau |
| 10,799,497 B2 | 10/2020 | Tabuteau |
| 10,806,710 B2 | 10/2020 | Tabuteau |
| 10,813,924 B2 | 10/2020 | Tabuteau |
| 10,864,209 B2 | 12/2020 | Tabuteau |
| 10,874,663 B2 | 12/2020 | Tabuteau |
| 10,874,664 B2 | 12/2020 | Tabuteau |
| 10,874,665 B2 | 12/2020 | Tabuteau |
| 10,881,624 B2 | 1/2021 | Tabuteau |
| 10,881,657 B2 | 1/2021 | Tabuteau |
| 10,894,046 B2 | 1/2021 | Tabuteau |
| 10,894,047 B2 | 1/2021 | Tabuteau |
| 10,898,453 B2 | 1/2021 | Tabuteau |
| 10,925,842 B2 | 2/2021 | Tabuteau |
| 10,933,034 B2 | 3/2021 | Tabuteau |
| 10,940,124 B2 | 3/2021 | Tabuteau |
| 10,945,973 B2 | 3/2021 | Tabuteau |
| 10,966,941 B2 | 4/2021 | Tabuteau |
| 10,966,942 B2 | 4/2021 | Tabuteau |
| 10,966,974 B2 | 4/2021 | Tabuteau |
| 10,980,800 B2 | 4/2021 | Tabuteau |
| 11,007,189 B2 | 5/2021 | Tabuteau |
| 11,020,389 B2 | 6/2021 | Tabuteau |
| 11,058,648 B2 | 7/2021 | Tabuteau |
| 11,065,248 B2 | 7/2021 | Tabuteau |
| 11,090,300 B2 | 8/2021 | Tabuteau |
| 11,096,937 B2 | 8/2021 | Tabuteau |
| 11,123,343 B2 | 9/2021 | Tabuteau |
| 11,123,344 B2 | 9/2021 | Tabuteau |
| 11,129,826 B2 | 9/2021 | Tabuteau |
| 11,141,388 B2 | 10/2021 | Tabuteau |
| 11,141,416 B2 | 10/2021 | Tabuteau |
| 11,147,808 B2 | 10/2021 | Tabuteau |
| 11,185,515 B2 | 11/2021 | Tabuteau |
| 11,191,739 B2 | 12/2021 | Tabuteau |
| 11,197,839 B2 | 12/2021 | Tabuteau |
| 11,207,281 B2 | 12/2021 | Tabuteau |
| 11,213,521 B2 | 1/2022 | Tabuteau |
| 11,229,640 B2 | 1/2022 | Tabuteau |
| 11,234,946 B2 | 2/2022 | Tabuteau |
| 11,253,491 B2 | 2/2022 | Tabuteau |
| 11,253,492 B2 | 2/2022 | Tabuteau |
| 11,273,133 B2 | 3/2022 | Tabuteau |
| 11,273,134 B2 | 3/2022 | Tabuteau |
| 11,285,118 B2 | 3/2022 | Tabuteau |
| 11,285,146 B2 | 3/2022 | Tabuteau |
| 11,291,638 B2 | 4/2022 | Tabuteau |
| 11,291,665 B2 | 4/2022 | Tabuteau |
| 11,298,351 B2 | 4/2022 | Tabuteau |
| 11,298,352 B2 | 4/2022 | Tabuteau |
| 11,311,534 B2 | 4/2022 | Tabuteau |
| 11,344,544 B2 | 5/2022 | Tabuteau |
| 11,357,744 B2 | 6/2022 | Tabuteau |
| 11,364,233 B2 | 6/2022 | Tabuteau |
| 11,382,874 B2 | 7/2022 | Tabuteau |
| 11,419,867 B2 | 8/2022 | Tabuteau |
| 11,426,370 B2 | 8/2022 | Tabuteau |
| 11,426,401 B2 | 8/2022 | Tabuteau |
| 11,433,067 B2 | 9/2022 | Tabuteau |
| 11,439,636 B1 | 9/2022 | Tabuteau |
| 11,478,468 B2 | 10/2022 | Tabuteau |
| 11,497,721 B2 | 11/2022 | Tabuteau |
| 11,510,918 B2 | 11/2022 | Tabuteau |
| 11,517,542 B2 | 12/2022 | Tabuteau |
| 11,517,543 B2 | 12/2022 | Tabuteau |
| 11,517,544 B2 | 12/2022 | Tabuteau |
| 11,524,007 B2 | 12/2022 | Tabuteau |
| 11,524,008 B2 | 12/2022 | Tabuteau |
| 11,534,414 B2 | 12/2022 | Tabuteau |
| 11,541,021 B2 | 1/2023 | Tabuteau |
| 11,541,048 B2 | 1/2023 | Tabuteau |
| 11,571,399 B2 | 2/2023 | Tabuteau |
| 11,571,417 B2 | 2/2023 | Tabuteau |
| 11,576,877 B2 | 2/2023 | Tabuteau |
| 11,576,909 B2 | 2/2023 | Tabuteau |
| 11,590,124 B2 | 2/2023 | Tabuteau |
| 11,596,627 B2 | 3/2023 | Tabuteau |
| 11,617,728 B2 | 4/2023 | Tabuteau |
| 11,617,747 B2 | 4/2023 | Tabuteau |
| 11,628,149 B2 | 4/2023 | Tabuteau |
| 11,660,273 B2 | 5/2023 | Tabuteau |
| 11,660,274 B2 | 5/2023 | Tabuteau |
| 11,717,518 B1 | 8/2023 | Tabuteau |
| 11,730,706 B1 | 8/2023 | Tabuteau |
| 11,752,144 B1 | 9/2023 | Tabuteau |
| 11,779,579 B2 | 10/2023 | Tabuteau |
| 11,839,612 B1 | 12/2023 | Tabuteau |
| 11,844,797 B1 | 12/2023 | Tabuteau |
| 11,883,373 B1 | 1/2024 | Tabuteau |
| 11,896,563 B2 | 2/2024 | Tabuteau |
| 11,925,636 B2 | 3/2024 | Tabuteau |
| 11,969,421 B2 | 4/2024 | Tabuteau |
| 11,986,444 B2 | 5/2024 | Tabuteau |
| 12,036,191 B1 | 7/2024 | Tabuteau |
| 12,042,473 B2 | 7/2024 | Tabuteau |
| 12,109,178 B2 | 10/2024 | Tabuteau |
| 12,138,260 B2 | 11/2024 | Tabuteau |
| 12,146,889 B1 | 11/2024 | Tabuteau |
| 12,156,914 B2 | 12/2024 | Tabuteau |
| 12,194,005 B2 | 1/2025 | Tabuteau |
| 12,194,006 B2 | 1/2025 | Tabuteau |
| 12,194,036 B2 | 1/2025 | Tabuteau |
| 2002/0035105 A1 | 3/2002 | Caruso |
| 2003/0044462 A1 | 3/2003 | Subramanian et al. |
| 2008/0044462 A1 | 2/2008 | Trumbore et al. |
| 2010/0040679 A1 | 2/2010 | Chang |
| 2010/0291225 A1 | 11/2010 | Fanda et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |
| 2015/0133486 A1 | 5/2015 | Tabuteau |
| 2015/0150830 A1 | 6/2015 | Tabuteau |
| 2015/0157582 A1 | 6/2015 | Tabuteau |
| 2015/0342947 A1 | 12/2015 | Pollard et al. |
| 2016/0008352 A1* | 1/2016 | Tabuteau ............. A61K 31/138 514/289 |
| 2016/0030420 A1 | 2/2016 | Tabuteau |
| 2016/0030421 A1 | 2/2016 | Tabuteau |
| 2016/0128944 A1 | 5/2016 | Chawrai et al. |
| 2016/0128998 A1* | 5/2016 | Tabuteau ............. A61K 31/137 514/289 |
| 2016/0136155 A1 | 5/2016 | Tabuteau |
| 2016/0199321 A1 | 7/2016 | Tabuteau |
| 2016/0228390 A1 | 8/2016 | Tabuteau |
| 2016/0263099 A1 | 9/2016 | Tabuteau |
| 2016/0263100 A1 | 9/2016 | Tabuteau |
| 2016/0317475 A1 | 11/2016 | Tabuteau |
| 2016/0317476 A1 | 11/2016 | Tabuteau |
| 2016/0324807 A1 | 11/2016 | Tabuteau |
| 2016/0339017 A1 | 11/2016 | Tabuteau |
| 2016/0346276 A1 | 12/2016 | Tabuteau |
| 2016/0361305 A1 | 12/2016 | Tabuteau |
| 2016/0375008 A1 | 12/2016 | Tabuteau |
| 2016/0375012 A1 | 12/2016 | Tabuteau |
| 2017/0007558 A1 | 1/2017 | Tabuteau |
| 2017/0014357 A1 | 1/2017 | Tabuteau |
| 2017/0252309 A1 | 9/2017 | Tabuteau |
| 2017/0281617 A1 | 10/2017 | Tabuteau |
| 2017/0304229 A1 | 10/2017 | Tabuteau |
| 2017/0304230 A1 | 10/2017 | Tabuteau |
| 2017/0304298 A1 | 10/2017 | Tabuteau |
| 2017/0354619 A1 | 12/2017 | Tabuteau |
| 2017/0360773 A1 | 12/2017 | Tabuteau |
| 2017/0360774 A1 | 12/2017 | Tabuteau |
| 2017/0360776 A1 | 12/2017 | Tabuteau |

(56) References Cited

U.S. PATENT DOCUMENTS

| | | |
|---|---|---|
| 2018/0092906 A1 | 4/2018 | Tabuteau |
| 2018/0116980 A1 | 5/2018 | Tabuteau |
| 2018/0133195 A1 | 5/2018 | Tabuteau |
| 2018/0207151 A1 | 7/2018 | Tabuteau |
| 2018/0256518 A1 | 9/2018 | Tabuteau |
| 2018/0360823 A1 | 12/2018 | Tabuteau |
| 2019/0000835 A1 | 1/2019 | Tabuteau |
| 2019/0008800 A1 | 1/2019 | Tabuteau |
| 2019/0008801 A1 | 1/2019 | Tabuteau |
| 2019/0008805 A1 | 1/2019 | Tabuteau |
| 2019/0015407 A1 | 1/2019 | Tabuteau |
| 2019/0083426 A1 | 3/2019 | Tabuteau |
| 2019/0142768 A1 | 5/2019 | Tabuteau |
| 2019/0192450 A1 | 6/2019 | Tabuteau |
| 2019/0192507 A1 | 6/2019 | Tabuteau |
| 2019/0216798 A1 | 7/2019 | Tabuteau |
| 2019/0216800 A1 | 7/2019 | Tabuteau |
| 2019/0216801 A1 | 7/2019 | Tabuteau |
| 2019/0290601 A1 | 9/2019 | Tabuteau |
| 2020/0022929 A1 | 1/2020 | Tabuteau |
| 2020/0093762 A1 | 3/2020 | Tabuteau |
| 2020/0147008 A1 | 5/2020 | Tabuteau |
| 2020/0147075 A1 | 5/2020 | Tabuteau |
| 2020/0197388 A1* | 6/2020 | Bear ................... A61P 3/04 |
| 2020/0206217 A1 | 7/2020 | Tabuteau |
| 2020/0215055 A1 | 7/2020 | Tabuteau |
| 2020/0215056 A1 | 7/2020 | Tabuteau |
| 2020/0215057 A1 | 7/2020 | Tabuteau |
| 2020/0215058 A1 | 7/2020 | Tabuteau |
| 2020/0215059 A1 | 7/2020 | Tabuteau |
| 2020/0222389 A1 | 7/2020 | Tabuteau |
| 2020/0230078 A1 | 7/2020 | Tabuteau |
| 2020/0230129 A1 | 7/2020 | Tabuteau |
| 2020/0230130 A1 | 7/2020 | Tabuteau |
| 2020/0230131 A1 | 7/2020 | Tabuteau |
| 2020/0237751 A1 | 7/2020 | Tabuteau |
| 2020/0237752 A1 | 7/2020 | Tabuteau |
| 2020/0246280 A1 | 8/2020 | Tabuteau |
| 2020/0261431 A1 | 8/2020 | Tabuteau |
| 2020/0297666 A1 | 9/2020 | Tabuteau |
| 2020/0338022 A1 | 10/2020 | Tabuteau |
| 2020/0360310 A1 | 11/2020 | Tabuteau |
| 2020/0397723 A1 | 12/2020 | Tabuteau |
| 2020/0397724 A1 | 12/2020 | Tabuteau |
| 2020/0405664 A1 | 12/2020 | Tabuteau |
| 2021/0000763 A1 | 1/2021 | Tabuteau |
| 2021/0000764 A1 | 1/2021 | Tabuteau |
| 2021/0000765 A1 | 1/2021 | Tabuteau |
| 2021/0000768 A1 | 1/2021 | Tabuteau |
| 2021/0000820 A1 | 1/2021 | Tabuteau |
| 2021/0015768 A1 | 1/2021 | Tabuteau |
| 2021/0015814 A1 | 1/2021 | Tabuteau |
| 2021/0015815 A1 | 1/2021 | Tabuteau |
| 2021/0023075 A1 | 1/2021 | Tabuteau |
| 2021/0023076 A1 | 1/2021 | Tabuteau |
| 2021/0030747 A1 | 2/2021 | Tabuteau |
| 2021/0030749 A1 | 2/2021 | Tabuteau |
| 2021/0030750 A1 | 2/2021 | Tabuteau |
| 2021/0030751 A1 | 2/2021 | Tabuteau |
| 2021/0046067 A1 | 2/2021 | Tabuteau |
| 2021/0052521 A1 | 2/2021 | Tabuteau |
| 2021/0060004 A1 | 3/2021 | Tabuteau |
| 2021/0060005 A1 | 3/2021 | Tabuteau |
| 2021/0069125 A1 | 3/2021 | Tabuteau |
| 2021/0069128 A1 | 3/2021 | Tabuteau |
| 2021/0077428 A1 | 3/2021 | Tabuteau |
| 2021/0077429 A1 | 3/2021 | Tabuteau |
| 2021/0077483 A1 | 3/2021 | Tabuteau |
| 2021/0106546 A1 | 4/2021 | Tabuteau |
| 2021/0177834 A1 | 6/2021 | Tabuteau |
| 2021/0186899 A1 | 6/2021 | Tabuteau |
| 2021/0186900 A1 | 6/2021 | Tabuteau |
| 2021/0186901 A1 | 6/2021 | Tabuteau |
| 2021/0186955 A1 | 6/2021 | Tabuteau |
| 2021/0186956 A1 | 6/2021 | Tabuteau |
| 2021/0196704 A1 | 7/2021 | Tabuteau |
| 2021/0196705 A1 | 7/2021 | Tabuteau |
| 2021/0205239 A1 | 7/2021 | Tabuteau |
| 2021/0205240 A1 | 7/2021 | Tabuteau |
| 2021/0205297 A1 | 7/2021 | Tabuteau |
| 2021/0220293 A1 | 7/2021 | Tabuteau |
| 2021/0220294 A1 | 7/2021 | Tabuteau |
| 2021/0220348 A1 | 7/2021 | Tabuteau |
| 2021/0260054 A1 | 8/2021 | Tabuteau |
| 2021/0267967 A1 | 9/2021 | Tabuteau |
| 2021/0338605 A1 | 11/2021 | Tabuteau |
| 2021/0346370 A1 | 11/2021 | Tabuteau |
| 2021/0361645 A1 | 11/2021 | Tabuteau |
| 2021/0401828 A1 | 12/2021 | Tabuteau |
| 2021/0401829 A1 | 12/2021 | Tabuteau |
| 2021/0401830 A1 | 12/2021 | Tabuteau |
| 2021/0401831 A1 | 12/2021 | Tabuteau |
| 2022/0008363 A1 | 1/2022 | Tabuteau |
| 2022/0071930 A1 | 3/2022 | Tabuteau |
| 2022/0071931 A1 | 3/2022 | Tabuteau |
| 2022/0079892 A1 | 3/2022 | Tabuteau |
| 2022/0096462 A1 | 3/2022 | Tabuteau |
| 2022/0105086 A1 | 4/2022 | Tabuteau |
| 2022/0133655 A1 | 5/2022 | Tabuteau |
| 2022/0142950 A1 | 5/2022 | Tabuteau |
| 2022/0193012 A1 | 6/2022 | Tabuteau |
| 2022/0218631 A1 | 7/2022 | Tabuteau |
| 2022/0218698 A1 | 7/2022 | Tabuteau |
| 2022/0233470 A1 | 7/2022 | Tabuteau |
| 2022/0233474 A1 | 7/2022 | Tabuteau |
| 2022/0233518 A1 | 7/2022 | Tabuteau |
| 2022/0233519 A1 | 7/2022 | Tabuteau |
| 2022/0241220 A1 | 8/2022 | Tabuteau |
| 2022/0241221 A1 | 8/2022 | Tabuteau |
| 2022/0241269 A1 | 8/2022 | Tabuteau |
| 2022/0241270 A1 | 8/2022 | Tabuteau |
| 2022/0265639 A1 | 8/2022 | Tabuteau |
| 2022/0280504 A1 | 9/2022 | Tabuteau |
| 2022/0313689 A1 | 10/2022 | Tabuteau |
| 2022/0323381 A1 | 10/2022 | Tabuteau |
| 2022/0378779 A1 | 12/2022 | Tabuteau |
| 2023/0045675 A1 | 2/2023 | Tabuteau |
| 2023/0096437 A1 | 3/2023 | Tabuteau |
| 2023/0099206 A1 | 3/2023 | Tabuteau |
| 2023/0100008 A1 | 3/2023 | Tabuteau |
| 2023/0100913 A1 | 3/2023 | Tabuteau |
| 2023/0114111 A1 | 4/2023 | Tabuteau |
| 2023/0131854 A1 | 4/2023 | Tabuteau |
| 2023/0142244 A1 | 5/2023 | Tabuteau |
| 2023/0210843 A1 | 7/2023 | Tabuteau |
| 2023/0218550 A1 | 7/2023 | Tabuteau |
| 2023/0225995 A1 | 7/2023 | Tabuteau |
| 2023/0233491 A1 | 7/2023 | Tabuteau |
| 2023/0241010 A1 | 8/2023 | Tabuteau |
| 2023/0248668 A1 | 8/2023 | Tabuteau |
| 2023/0248669 A1 | 8/2023 | Tabuteau |
| 2023/0255905 A1 | 8/2023 | Tabuteau |
| 2023/0263750 A1 | 8/2023 | Tabuteau |
| 2023/0270740 A1 | 8/2023 | Tabuteau |
| 2023/0277478 A1 | 9/2023 | Tabuteau |
| 2023/0277479 A1 | 9/2023 | Tabuteau |
| 2023/0277480 A1 | 9/2023 | Tabuteau |
| 2023/0277481 A1 | 9/2023 | Tabuteau |
| 2023/0293456 A1 | 9/2023 | Tabuteau |
| 2024/0000770 A1 | 1/2024 | Tabuteau |
| 2024/0016797 A1 | 1/2024 | Tabuteau |
| 2024/0024309 A1 | 1/2024 | Tabuteau |
| 2024/0041862 A1 | 2/2024 | Tabuteau |
| 2024/0041863 A1 | 2/2024 | Tabuteau |
| 2024/0050383 A1 | 2/2024 | Tabuteau |
| 2024/0066025 A1 | 2/2024 | Tabuteau |
| 2024/0115524 A1 | 4/2024 | Tabuteau |
| 2024/0148719 A1 | 5/2024 | Tabuteau |
| 2024/0156751 A1 | 5/2024 | Tabuteau |
| 2024/0165104 A1 | 5/2024 | Tabuteau |
| 2024/0189302 A1 | 6/2024 | Tabuteau |
| 2024/0197656 A1 | 6/2024 | Tabuteau |
| 2024/0197720 A1 | 6/2024 | Tabuteau |
| 2024/0238276 A1 | 7/2024 | Tabuteau |

(56) References Cited

U.S. PATENT DOCUMENTS

| | | |
|---|---|---|
| 2024/0252451 A1 | 8/2024 | Tabuteau |
| 2024/0269130 A1 | 8/2024 | Tabuteau |
| 2024/0299319 A1 | 9/2024 | Tabuteau |
| 2024/0299320 A1 | 9/2024 | Tabuteau |
| 2024/0307408 A1 | 9/2024 | Tabuteau |
| 2024/0390297 A1 | 11/2024 | Tabuteau |
| 2024/0408040 A1 | 12/2024 | Tabuteau |
| 2025/0009754 A1 | 1/2025 | Tabuteau |
| 2025/0012821 A1 | 1/2025 | Tabuteau |

FOREIGN PATENT DOCUMENTS

| | | |
|---|---|---|
| KR | 101612197 B1 | 4/2016 |
| WO | 1998050044 | 11/1998 |
| WO | 2003086362 A2 | 10/2003 |
| WO | 2004089873 A1 | 10/2004 |
| WO | 2009006194 | 1/2009 |
| WO | 2009050726 A2 | 4/2009 |
| WO | 2015069809 A1 | 5/2015 |
| WO | 2016125108 A1 | 8/2016 |
| WO | 2020146412 A1 | 7/2020 |
| WO | 2021202329 A1 | 10/2021 |
| WO | 2021202419 A1 | 10/2021 |
| WO | 2022119981 A1 | 6/2022 |
| WO | 2023004064 A1 | 1/2023 |

OTHER PUBLICATIONS

Auvelity (dextromethorphan hydrobromide and bupropion hydrochloride), Highlights of Prescribing Information and Medication Guide, issued Dec. 2022.

International Preliminary Report on Patentability, PCT/US2021/061492, mailed on Jun. 15, 2023.

International Search Report and Written Opinion, PCT/US2021/061492 received on Jun. 15, 2023.

International Search Report and Written Opinion, PCT/US2022/012768 received on Jul. 5, 2023.

International Search Report and Written Opinion, PCT/US2023/067062 mailed on Jul. 12, 2023.

Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.

Anderson, A.; et al. "Efficacy and Safety of AXS-05, an Oral NMDA Receptor Antagonist with Multimodal Activity, in Major Depressive Disorder: Results of a Phase 2, Double-Blind, Active-Controlled Trial" ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).

O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).

O'Gorman, C.; et al. "PMH40 Effects of AXS-05 on Patient Reported Depressive Symptoms in Major Depressive Disorder: Results from the Gemini Trial" <doi.org/10.1016/j.jval.2021.04.662> (retrieved from internet on Jul. 19, 2023). Value in Health, Jun. 2021, vol. 24, Supplement 1, pp. S135.

O'Gorman, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.

International Preliminary Report on Patentability, PCT/US2022/012768, mailed on Jul. 27, 2023.

Nofziger et al., Evaluation of dextromethorphan with select antidepressant therapy for the treatment of depression in the acute care psychiatric setting, Mental Health Clinician, 9(2), 76-81, Mar. 2019.

Update: Bupropion Hydrochloride Extended-Release 300 mg Bioequivalence Studies, FDA, retrieved Mar. 2021.

FDA Draft Guidance on Bupropion Hydrochloride, revised Mar. 2013.

Forfivo XL (bupropion hydrochloride) extended-release tablets, for oral use, Highlights of Prescribing Information, revised Dec. 2019.

Forfivo XL (Bupropion HCI) extended-release tablet, NDA 22497, Jan. 25, 2010.

Wellbutrin XL (bupropion hydrochloride extended-release), Highlights of Prescribing Information, revised Mar. 2022.

Baker T. E. et al., Human Milk and Plasma Pharmacokinetics of Single-Dose Rimegepant 75mg in Healthy Lactating Women, Breastfeeding Medicine, 17(3), 277-282, 2022.

Berle J. O. et al., Antidepressant Use During Breastfeeding, Current Women's Health Reviews, 7(1), 28-34, Feb. 2011.

Briggs G. G. et al., Excretion of bupropion in breast milk, Annals of Pharmacotherapy, 27(4):431-433, Apr. 1993.

Chad L. et al., Update on antidepressant use during breastfeeding, Canadian Family Physician, 59(6), 633-634, Jun. 2013.

Chaudron L. H. et al., Bupropion and Breastfeeding: A case of a possible Infant Seizure, The Journal of clinical psychiatry, 65(6), 881-882, Jun. 2004.

Davis M. F. et al., Bupropion Levels in Breast Milk for 4 Mother-Infant Pairs: More Answers to Lingering Questions, J. Clin. Psychiatry, 70(2), 297-298, Feb. 2009.

Di Scalea T. L. et al., Antidepressant Medication Use during Breastfeeding, Clinical obstetrics and gynecology, 52 (3): 483-497, Sep. 2009.

Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.

Gentile S, The safety of newer antidepressants in pregnancy and breastfeeding, Drug Safety, 28(2), 137-152, Feb. 2005. [doi: 10.2165/00002018-200528020-00005. PMID: 15691224.].

Haas J. S. et al., Bupropion in breast milk: an exposure assessment for potential treatment to prevent post-partum tobacco use, Tobacco Control, 13(1), 52-56, Mar. 2004.

Ram D. et al., Antidepressants, anxiolytics, and hypnotics in pregnancy and lactation, Indian J Psychiatry, 57(Suppl 2): S354-S371, Jul. 2015. [doi:10.4103/0019-5545.161504].

Weissman A. M. et al., Pooled Analysis of Antidepressant Levels in Lactating Mothers, Breast Milk, and Nursing Infants, Am J Psychiatry, 161(6), 1066-1078, Jun. 2004.

Horn J. R. et al., Get to Know an Enzyme: CYP2D6, Pharmacy Times, Jul. 2008, retrieved on Aug. 28, 2023.

International Search Report and Written Opinion, PCT/US2023/069286 mailed on Aug. 22, 2023.

International Search Report and Written Opinion, PCT/US2023/069239 mailed on Aug. 28, 2023.

International Search Report and Written Opinion, PCT/US2023/069367 mailed on Aug. 28, 2023.

International Search Report and Written Opinion, PCT/US2023/069655 mailed on Sep. 15, 2023.

International Search Report and Written Opinion, PCT/US2023/069371 mailed on Sep. 26, 2023.

International Search Report and Written Opinion, PCT/US2022/037913 mailed on Sep. 21, 2022.

Jones A et al., "Early Improvements in Functioning and Quality of Life With AXS-05 in Major Depressive Disorder: Results From the Gemini Trial ," Value in Health, Jun. 2021, vol. 24, abstract No. PHM42, p. S135. Doi:10.1016/j.jval.2021.04.662.

International Search Report and Written Opinion, PCT/US2022/074713 mailed on Sep. 21, 2022.

Axsome Therapeutics, Inc.: "Merit: A Randomized, Double-blind, Placebo-controlled Study of AXS-05 for Relapse Prevention in Treatment Resistant Depression," ClinicalTrials.gov, NCT04608396 version 2, Mar. 24, 2021.

International Preliminary Report on Patentability, PCT/US2022/037913, issued on Jan. 18, 2024.

(56) References Cited

OTHER PUBLICATIONS

International Preliminary Report on Patentability, PCT/US2022/074713, issued on Feb. 22, 2024.
Chinese Pat. No. 202080004041.1 Invalidation Notice and Request issued on Jan. 15, 2024. (English translation included).
Ward K. and Citrome L.: "AXS-05: an investigational treatment for Alzheimer's disease-associated agitation", Expert Opinion on Investigational Drugs, Jul. 6, 2022, vol. 31, issue 8, pp. 773-780, DOI: 10.1080/13543784.2022.2096006.
Defendant Teva Pharmaceuticals, Inc.'s Invalidity Contentions for U.S. Pat. Nos. 11,752,144, 11,717,518, 11,730,706 and Exhibits A-C dated Apr. 11, 2024.
Goodnick, Psychotropic drugs and the ECG: focus on the QTc interval, Expert Opinion on Pharmacotherapy, vol. 3, No. 5, p. 479-498, 2002.
International Search Report and Written Opinion, PCT/US2024/046359 mailed on Nov. 28, 2024.
Tabuteau H, et al. "Effect of AXS-05 (Dextromethorphan-Bupropion) in Major Depressive Disorder: A Randomized Double-Blind Controlled Trial" Am J Psychiatry (2022) vol. 179 pp. 490-499. doi: 10.1176/appi.ajp.21080800.
International Preliminary Report on Patentability, PCT/US2023/067062, mailed on Nov. 28, 2024.
International Search Report and Written Opinion, PCT/US2024/043903 mailed on Nov. 28, 2024.
International Preliminary Report on Patentability, PCT/US2023/069286, mailed on Jan. 9, 2025.
International Preliminary Report on Patentability, PCT/US2023/069371, mailed on Jan. 9, 2025.
International Preliminary Report on Patentability, PCT/US2023/069655, mailed on Jan. 16, 2025.

\* cited by examiner

PHARMACEUTICAL COMPOSITIONS COMPRISING BUPROPION AND CYSTEINE

CROSS REFERENCE TO RELATED APPLICATIONS

This application claims the benefit of U.S. Provisional Pat. App. No. 63/578,241, filed Aug. 23, 2023; which is incorporated by reference in its entirety.

BACKGROUND

Bupropion is FDA approved for the treatment of depression and for smoking cessation.

SUMMARY

This disclosure relates to pharmaceutical compositions, and dosage forms containing bupropion and cysteine, and uses of such compositions and dosage forms. The disclosure also relates to molecular complexes of bupropion and cysteine.

Some embodiments, including embodiments containing a molecular complex of bupropion and cysteine, have a molar ratio of bupropion to cysteine of about 0.9:1 to about 1.1:1. These molecular complexes may be more stable than bupropion alone.

Some embodiments include a pharmaceutical composition comprising a molecular complex of bupropion and cysteine, wherein the molar ratio of bupropion to cysteine in the molecular complex is about 0.5:1 to about 2:1 or about 0.9:1 to about 1.1:1. These pharmaceutical compositions may be more stable than a similar pharmaceutical composition having bupropion without cysteine.

Some embodiments include a pharmaceutical dosage form comprising bupropion and cysteine, possibly including a molecular complex of bupropion and cysteine, wherein the dosage form comprises about 90 mg to about 120 mg of bupropion and about 30 mg to about 100 mg of cysteine.

DETAILED DESCRIPTION

This disclosure relates to a pharmaceutical composition comprising bupropion and cysteine. It has been found that cysteine in the amounts described herein is effective in stabilizing bupropion in the presence of common excipients such as calcium phosphate, methylcellulose, hydroxypropylmethylcelluloses, sodium carboxycellulose, etc.

A pharmaceutical composition, dosage form, or molecular complex, may include, or be prepared from, any suitable form of bupropion, such as a salt form, e.g., bupropion hydrochloride, the free base form, hydrates, solvates, polymorphs, other solid forms, etc. In some embodiments, the pharmaceutical composition is free of any other active pharmaceutical agents.

The pharmaceutical dosage form may include any suitable amount of bupropion, such as about 80-150 mg, about 80-120 mg, about 80-90 mg, about 90-100 mg, about 100-110 mg, about 110-120 mg, about 103-107 mg, or about 105 mg of the bupropion, such as bupropion hydrochloride, another salt form of bupropion, or the free base form of bupropion.

A pharmaceutical composition, dosage form, or molecular complex, may include, or be prepared from, any suitable form of cysteine, such as a neutral form, a zwitterionic form, a salt form, e.g., cysteine hydrochloride, hydrates, solvates, polymorphs, other solid forms, etc.

The pharmaceutical composition may include any suitable amount of cysteine (e.g., L-cysteine), such as about 30-100 mg, about 30-40 mg, about 40-50 mg, about 50-60 mg, about 60-70 mg, about 70-80 mg, about 80-90 mg, about 90-100 mg, about 65-70 mg, or about 67 mg of the cysteine, such as L-cysteine hydrochloride, another salt form of L-cysteine, or the neutral or zwitterionic form of L-cysteine. Cysteine in these amounts may be helpful in stabilizing bupropion in the presence of other excipients. The cysteine may be in the form of a hydrate of cysteine. For example, the cysteine may be in the form of a hydrate. For example, the cysteine may be in the form of cysteine hydrochloride monohydrate or L-cysteine hydrochloride monohydrate.

In some pharmaceutical compositions, bupropion and cysteine may be in the form of a molecular complex, or may be non-covalently bound or associated with one another, molecular complexes include both salts and other forms of non-covalent binding interactions such as hydrogen bonding, van der Waals interactions, etc.

One potential bupropion-cysteine molecular complex is represented by a structure:

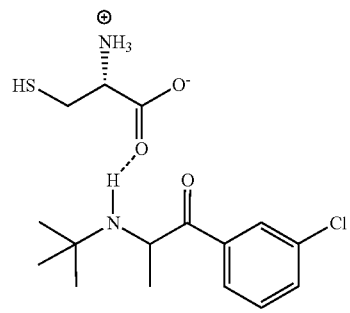

In some embodiments, the molar ratio of bupropion to cysteine may be about 0.2:1 (e.g. 0.2 moles of bupropion to 1 mole of cysteine) to about 4:1, about 0.2:1 to about 0.5:1, about 0.5:1 to about 0.7:1 about 0.7:1 to about 0.9:1, about 0.9:1 to about 1.1:1, about 1.1:1 to about 1.3:1, about 1.3:1 to about 1.5:1, about 1.5:1 to about 2:1, about 2:1 to about 3:1, about 3:1 to about 4:1, about 0.5:1, or about 1:1.

The pharmaceutical composition or dosage form may further comprise a sustained release or controlled release polymer, such as a crosslinked or uncross linked acrylate polymer or copolymer (e.g., a carbomer copolymer Type A such as Carbopol 971P), a cellulose derivative, such as methylcellulose, etc. In some embodiments, the controlled release polymer is about 1-40%, about 1-5%, about 5-10%, about 10-15%, about 15-20%, about 20-30%, about 30-40%, about 11-13%, or about 12% of the weight of the pharmaceutical composition. In some embodiments, the controlled release polymer is about 0.1-20%, about 0.1-2%, about 2-4%, about 4-6%, about 6-8%, about 8-10%, about 10-15%, about 15-20%, or about 7% of the weight of the dosage form.

The pharmaceutical composition or dosage form may further comprise a filler such as microcrystalline cellulose. In some embodiments, the filler may be about 20-60%, about 20-30%, about 30-40%, about 40-50%, or about 50-60% of the weight of the pharmaceutical composition or the dosage form.

The pharmaceutical composition or dosage form may further comprise a lubricant such as magnesium stearate. In some embodiments, the lubricant is about 0.1-10%, about 0.1-2%, about 2-4%, about 4-6%, about 6-8%, or about 8-10% of the weight of the pharmaceutical composition or the dosage form.

The dosage form may be formulated for any suitable route of administration, such as oral administration.

Dosage forms, such as solid dosage forms, e.g., capsules, tablets, or pills, for oral administration may also contain one or more of the following: a binder such as gum tragacanth, acacia, corn starch, or gelatin; an excipient, such as dicalcium phosphate; a disintegrating agent such as corn starch, potato starch, alginic acid, and the like; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as a coating, for example, tablets, pills, or capsules may be coated with shellac, sugar, or both. It may be desirable for material in a dosage form or pharmaceutical composition to be pharmaceutically pure and substantially nontoxic in the amounts employed.

The dosage form may further contain a second active pharmaceutical ingredient, such as dextromethorphan, e.g., dextromethorphan hydrochloride. In some embodiments, the dosage form may contain bupropion and dextromethorphan, and no other active pharmaceutical ingredients. In some embodiments, the bupropion and the dextromethorphan are in two different layers or phases of the dosage form, e.g., each layer contains only bupropion or dextromethorphan and none of the other.

In some embodiments, the dosage form contains cysteine, Carbopol 971P, microcrystalline cellulose, silicon dioxide, and magnesium. In some embodiments, the dosage form contains a first layer comprising bupropion and cysteine, and a second layer comprising dextromethorphan, microcrystalline cellulose, croscarmellose sodium, and magnesium stearate.

An example of a single layer dosage form is show below:

| Ingredient | Amount (mg) |
| --- | --- |
| Bupropion | 90-120 |
| Cysteine | 50-100 |
| Carbopol 971P | 20-60 |
| Microcrystalline Cellulose | 200-300 |
| Colloidal Silicon Dioxide | 1-10 |
| Magnesium Stearate | 1-10 |

A two layer dosage form may contain a first layer with the composition above, and a second layer detailed below.

| Layer 2 | |
| --- | --- |
| Ingredient | Amount (mg) |
| Dextromethorphan | 30-60 |
| Microcrystalline Cellulose | 100-150 |
| Croscarmellose sodium | 1-20 |
| Magnesium Stearate | 1-10 |

The pharmaceutical compositions, dosage forms, or molecular complexes described herein may be useful in treating neurological or psychiatric conditions, such as depression, including major depressive disorder or treatment-resistant major depressive disorder, agitation, such as agitation associated with Alzheimer's disease, addiction, such as nicotine addiction, etc.

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, Hitting (including self), Kicking, Grabbing onto people, Pushing, Throwing things, Biting, Scratching, Spitting, Hurting self or others, Tearing things or destroying property, Making physical sexual advances, Pacing, aimless wandering, Inappropriate dress or disrobing, Trying to get to a different place, Intentional falling, Eating/drinking inappropriate substances, Handling things inappropriately, Hiding things, Hoarding things, Performing repetitive mannerisms, General restlessness, Screaming, Making verbal sexual advances, Cursing or verbal aggression, Repetitive sentences or questions, Strange noises (weird laughter or crying), Complaining, Negativism, Constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, *cannabis* (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandhoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

Bupropion may not be stable in the presence of (or incompatible with) an excipient. Bupropion may be incompatible with many commonly used excipients including, but not limited to, dibasic calcium phosphate anhydrous, sodium carboxymethylcellulose, hydroxypropyl cellulose, hydroxyethylcellulose, croscarmellose sodium, or sodium starch glycolate. Methylcellulose or poly(acrylic acid) (PAA or Carbomer) may have low incompatibility as a release controlling polymer.

Bupropion in combination with ascorbic acid may be relatively stable. Cysteine may have a stabilizing effect on bupropion. The stability of bupropion in the presence of cysteine may be significantly higher as compared to ascorbic acid.

Dextromethorphan may pose no incompatibility issue with (or stable in the presence of) many commonly used excipients including, but not limited to, dibasic calcium phosphate anhydrous, hydroxypropyl cellulose, hydroxyethylcellulose, methylcellulose, poly(acrylic acid) (PAA or Carbomer), croscarmellose sodium, or sodium starch glycolate. Dextromethorphan may not be compatible with sodium carboxymethylcellulose. Dextromethorphan may not be stable in the presence of sodium carboxymethylcellulose.

In some embodiments, the molar ratio of bupropion to cysteine may affect the stability of the bupropion. The molar ratio of bupropion to cysteine of 1:2 may provide significantly higher stability of bupropion than the molar ratio of 1:0.5. The molar ratio of 1:1 may provide best stability.

The most stable mixture of bupropion and cysteine may be achieved using a 1:1 molar ratio of bupropion to cysteine. The most stable mixture of bupropion and ascorbic may be achieved using a 1:1 molar ratio of bupropion to ascorbic acid.

Bupropion in combination with dextromethorphan may exhibit good stability. A combination of bupropion and dextromethorphan may be in a form of a bilayer tablet.

In the formulation for a bilayer tablet comprising bupropion, cysteine, and dextromethorphan, the molar ratio of bupropion to cysteine that provides good stability of bupropion, may be about 1:1 to about 1:2, about 1:1, or about 1:2.

In some embodiments, a bilayer tablet may comprise 105 mg of bupropion hydrochloride, 45 mg of dextromethorphan hydrobromide, and cysteine hydrochloride monohydrate with the molar ratio of the bupropion to the cysteine of about 1:1 to about 1:2. In some embodiments, the bilayer tablet may further comprise Carbopol 971P, microcrystalline cellulose PH 101, microcrystalline cellulose PH 102, colloidal silicon dioxide (Cabosil M5P), magnesium stearate, or croscarmellose sodium, or a combination thereof. In some embodiments, the bilayer tablet may further comprise Carbopol 971P, microcrystalline cellulose PH 101, microcrystalline cellulose PH 102, colloidal silicon dioxide (Cabosil M5P), magnesium stearate, and croscarmellose sodium.

The term "treating" or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105, 361, 10,251,879, 10,463,634, 10,512,643, 10,548,857, 10,596,167, 10,772,850, 10,780,064, 10,780,066, 10,786, 469, 10,786,496, 10,799,497, 10,806,710, 10,864,209, 10,874,663, 10,874,664, 10,874,665, 10,881,624, 10,881, 657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

The following documents are incorporated by reference herein in their MEDICATION GUIDE for AUVELITY™ (www.axsome.com/auvelity-medication-entireties: guide.pdf), and HIGHLIGHTS OF PRESCRIBING INFORMATION for AUVELITY™ (www.axsome.com/auvelity-prescribing-information.pdf).

Specifically Contemplated Embodiments

The following are examples of embodiments that are specifically contemplated by the inventor:

Embodiment 1. A molecular complex of bupropion and cysteine, wherein the molecular complex is in solid form and has a molar ratio of bupropion to cysteine that is from about 0.5:1 to about 2:1.

Embodiment 2. The molecular complex of embodiment 1, wherein the molar ratio of bupropion to cysteine is about 0.9:1 to about 1.3:1.

Embodiment 3. A pharmaceutical composition comprising bupropion and cysteine, wherein the pharmaceutical composition is in a solid form, and the molar ratio of bupropion to cysteine is from about 0.5:1 to about 1.5:1.

Embodiment 4. The pharmaceutical composition of embodiment 3, wherein the molar ratio of bupropion to cysteine is about 0.9:1 to about 1.3:1.

Embodiment 5. The pharmaceutical composition of embodiment 3 or 4, further comprising a sustained release polymer.

Embodiment 6. The pharmaceutical composition of embodiment 5, wherein the sustained release polymer is an acrylate polymer or copolymer, a poly(acrylic acid), a methylcellulose, or a combination thereof.

Embodiment 7. The pharmaceutical composition of embodiment 3, 4, 5, or 6, further comprising a filler.

Embodiment 8. The pharmaceutical composition of embodiment 7, wherein the filler is microcrystalline cellulose.

Embodiment 9. A pharmaceutical dosage form comprising bupropion and cysteine, wherein the dosage form is a solid and comprises about 80 mg to about 120 mg of bupropion, and about 30 mg to about 100 mg of cysteine.

Embodiment 10. The pharmaceutical dosage form of embodiment 9, wherein the dosage form has a molar ratio of bupropion to cysteine that is about 0.5:1 to about 2:1.

Embodiment 11. The pharmaceutical dosage form of embodiment 9 or 10, wherein the molar ratio of bupropion to cysteine is about 1:1.

Embodiment 12. The pharmaceutical dosage form of embodiment 9, 10, or 11, further comprising a sustained release polymer.

Embodiment 13. The pharmaceutical dosage form of embodiment 12, wherein the sustained release polymer is an acrylate polymer or copolymer, a methylcellulose, or a combination thereof.

Embodiment 14. The pharmaceutical dosage form of embodiment 9, 10, 11, 12, or 13, which is in the form of a capsule, pill, or tablet.

Embodiment 15. The pharmaceutical dosage form of embodiment 9, 10, 11, 12, 13, or 14, wherein the dosage form further comprises dextromethorphan.

Embodiment 16. The pharmaceutical dosage form of embodiment 15, wherein the bupropion and the cysteine are in a first layer and the dextromethorphan is in a second layer.

Embodiment 17. The pharmaceutical dosage form of embodiment 9, 10, 11, 12, 13, 14, 15, or 16, further comprising a filler.

Embodiment 18. The pharmaceutical dosage form of embodiment 17, wherein the filler is microcrystalline cellulose.

Embodiment 19. The pharmaceutical dosage form of embodiment 9, 10, 11, 12, 13, 14, 15, 16, 17, or 18, further comprising a lubricant.

Embodiment 20. The pharmaceutical dosage form of embodiment 19, wherein the lubricant is magnesium stearate.

Embodiment 21. The pharmaceutical dosage form of embodiment 9, 10, 11, 12, 13, 14, 15, 16, 17, 18, 19, or 20, wherein the cysteine is L-cysteine hydrochloride monohydrate.

Embodiment 22. The molecular complex of bupropion and cysteine of embodiment 1 or 2, wherein the bupropion is more stable than bupropion alone.

Embodiment 23. The pharmaceutical dosage form of embodiment 9, 10, 11, 12, 13, 14, 15, 16, 17, 18, 19, 20, or 21, wherein the bupropion is more stable than bupropion alone.

Embodiment 24. A pharmaceutical composition comprising the molecular complex of embodiment 1 or 2.

Embodiment 25. The pharmaceutical composition of embodiment 3, wherein bupropion and cysteine form a molecular complex.

Embodiment 26. The molecular complex of embodiment 1, wherein the molar ratio of bupropion to cysteine is about 0.5:1 to about 1:1.

Embodiment 27. A pharmaceutical composition comprising the molecular complex of embodiment 26.

Embodiment 28. The pharmaceutical composition of embodiment 3, wherein the molar ratio of bupropion to cysteine is about 0.5:1 to about 1:1.

Example 1

INTRODUCTION

The scope of project 0328-150079-0001 was to develop two formulations containing Bupropion hydrochloride suitable for Phase III clinical studies. The first formulation was developed as a bilayer tablet for a combination of bupropion hydrochloride 105 mg (BUP105) and dextromethorphan hydrobromide monohydrate (DEX45) 45 mg. The second formulation was developed as bupropion hydrochloride 150 mg (BUP150) tablet using a common blend approach.

Design of Experiments

Formulation activities were initiated with excipient compatibility studies performed using a binary mixture of each API with known excipients typically used in solid dosage forms per Xcelience protocol #P328-001A. Significant compatibility issues were observed with bupropion hydrochloride with most of the excipients evaluated. The possible cause could be the absence of cysteine hydrochloride, which has shown to have a stabilizing effect on bupropion. A follow-up blend compatibility study was performed per protocol P0328-001B. Bupropion was observed to be stable in presence of cysteine hydrochloride in both studies. Based on these results prototype development was initiated with a top-spray granulation approach towards making a bilayer tablet for BUP105-DEX45 and a single layer tablet of BUP150 using a common blend approach for the bupropion hydrochloride portion.

Excipient Compatibility Study An excipient compatibility study was initiated using the excipients listed in Table 1. Commonly used excipients which were already a part of the currently available commercial products were not included in this study. Excipient compatibility samples were individually prepared as listed in Table 1 and placed at 25° C./60% RH, 40° C./75% RH and 50° C. in closed containers to avoid moisture penetration. These samples were pulled from the stability chambers per the schedule listed in Table 2 and tested for assay and related substances.

TABLE 1

Excipient compatibility samples

| Functionality | Material | Trade Name | Grade | Manufacturer | Mixture Ratio[a] Drug:Excipient |
|---|---|---|---|---|---|
| Fillers | Dibasic calcium phosphate anhydrous | Emcompress ® | USP/NF | JRS Pharma | 1:10 |
| Release controlling polymers | Sodium Carboxymethylcellulose | Aqualon ™ CMC 7MF PH | USP/NF | Ashland | 1:10 |
| | Hydroxypropylcellulose | Klucel ™ JXF PHARM | USP/NF | Ashland | 1:10 |
| | Hydroxyethylcellulose | Natrosol ™ 250HHX PHARM | USP/NF | Ashland | 1:10 |
| | Methylcellulose | Benecel ™ A4M PHARM | USP/NF | Dow | 1:10 |
| | Carbomer | Carbopol 971P | USP/NF | Lubrizol | 1:10 |
| Acidifiers | Cystein HCl | Cystein HCl | USP/NF | Spectrum Chemicals | 1:1 |
| | Ascorbic acid | Ascorbic acid | USP/NF | Spectrum Chemicals | 1:1 |
| Disintegrant | Croscarmellose sodium | Ac-Di-Sol | USP/NF | FMC Biopolymer | 1:1 |
| | Sodium starch glycolate | Explotab ® | USP/NF | JRS Pharma | 1:1 |

[a]Ratio refers to molar ratio.

TABLE 2

Excipient compatibility schedule

| Time Points | Initial | 2 Weeks | 4 Weeks | 8 Weeks |
|---|---|---|---|---|
| Conditions | NA | 25° C./60% RH (Storage only) 40° C./75% RH 50° C./ambient (Storage only) | 25° C./60% RH 40° C./75% RH 50° C./ambient | 25° C./60% RH 40° C./75% RH 50° C./ambient (Storage only) |

Note:
RH represents relative humidity.

The results from the excipient compatibility study have been compiled in Table 3 and Table 4. The level of impurities at each time point compared to initial (t=0) was used as an indication of compatibility issues, based on which, following observations were made.

Bupropion hydrochloride exhibited incompatibility with most of the excipients from the 2 week time point, with total impurities significantly higher than t=0.

Samples containing bupropion hydrochloride only and a combination of dextromethorphan hydrobromide monohydrate-bupropion hydrochloride were observed to be stable for the entire 8 weeks.

Samples containing bupropion hydrochloride in combination with cysteine hydrochloride and ascorbic acid were found to be relatively stable.

Amongst the five polymers tested, Methocel A4M and Carbopol 971P appeared to have the least incompatibility.

Dextromethorphan hydrobromide monohydrate was observed to be significantly more stable as compared to bupropion hydrochloride up to the 8 week time point. The low assay values observed were deemed sampling errors during sample prep or testing due to the nature of the experiment and were not examined any further.

TABLE 3

Excipient compatibility data for bupropion hydrochloride

| Sample ID | Sample | Time Point/ Cond | TOTAL RS > LOQ | | | | ASSAY | | | |
|---|---|---|---|---|---|---|---|---|---|---|
| | | | T = 0 | 2 wks | 4 wks | 8 wks | T = 0 | 2 wks | 4 wks | 8 wks |
| AB | Bupropion | 25/60 | <LOQ | | <LOQ | 0.13 | 100.4 | | 97.6 | 100.2 |
| | | 40/75 | | 0.43 | 0.94 | 1.16 | | 100.4 | 99.3 | 101.3 |
| | | 50 | | 0.14 | | | | 100.6 | | |
| BB | Bupropion Dextromethorphan | 25/60 | <LOQ | | 0.11 | 0.22 | 97.4 | | 98.9 | 97.3 |
| | | 40/75 | | 0.37 | 1.02 | 2.08 | | 98.4 | 101.3 | 99.7 |
| | | 50 | | 0.14 | | | | 100.2 | | |
| CB | Dibasic calcium phosphate anhydrous | 25/60 | <LOQ | | 2.91 | | 88.4 | | 87.4 | |
| | | 40/75 | | 8.76 | 14.43 | | | 85.4 | 92.7 | |
| | | 50 | | 15.33 | | | | 78.1 | | |
| DB | Sodium carboxymethyl cellulose 7MF PH | 25/60 | <LOQ | | 2.66 | | 83.6 | | 78.9 | |
| | | 40/75 | | 52.09 | 94.64 | | | 50.9 | 4.6 | |
| | | 50 | | 99.74 | | | | 0.1 | | |
| EB | Hydroxypropyl cellulose JXF | 25/60 | <LOQ | | 7.96 | | 75.1 | | 79.2 | |
| | | 40/75 | | 33.63 | 53.33 | | | 54.7 | 40.3 | |
| | | 50 | | 65.54 | | | | 35.1 | | |

TABLE 3-continued

Excipient compatibility data for bupropion hydrochloride

| Sample ID | Sample | Time Point/ Cond | TOTAL RS > LOQ | | | | ASSAY | | | |
|---|---|---|---|---|---|---|---|---|---|---|
| | | | T = 0 | 2 wks | 4 wks | 8 wks | T = 0 | 2 wks | 4 wks | 8 wks |
| FB | Hydroxyethyl-cellulose 250HHX | 25/60 40/75 50 | <LOQ | 24.42 46.80 | 7.55 30.13 | | 80.7 | 71.1 62.0 | 74.0 78.1 | |
| GB | Methyl-cellulose A4M | 25/60 40/75 50 | 0.34 | 1.83 6.22 | 0.46 4.44 | 0.89 8.62 | 67.2 | 91.5 92.2 | 82.1 75.8 | 90.4 89.4 |
| HB | Carbomer 971P | 25/60 40/75 50 | 1.03 | 1.65 1.85 | 1.56 2.05 | 2.05 3.40 | 47.1 | 48.7 | 69.1 48.3 | 81.7 34.6 |
| IB | Cysteine HCl | 25/60 40/75 50 | <LOQ | <LOQ <LOQ | 0.20 | ND ND | 87.0 | 75.8 | 87.1 80.1 | 87.7 84.8 |
| JB | Ascorbic Acid | 25/60 40/75 50 | <LOQ | <LOQ <LOQ | 0.18 0 | ND ND | 92.9 | 74.3 | 86.0 63.0 | 71.7 64.0 |
| KB | Croscarmellose sodium | 25/60 40/75 50 | 12.94 | 91.56 99.48 | 10.88 99.72 | | 78.5 | 15.0 | 92.0 0.1 | |
| LB | Sodium starch glycolate | 25/60 40/75 50 | 0.44 | 98.62 99.30 | 2.77 99.39 | | 91.1 | 1.1 | 95.8 0.1 | |

Note:
RS represents related substances. LOQ means Limit of Quantification.

TABLE 4

Excipient compatibility data for dextromethorphan hydrobromide monohydrate

| Sample ID | Sample | Time Point/ Condition | TOTAL RS | | | | ASSAY | | | |
|---|---|---|---|---|---|---|---|---|---|---|
| | | | T = 0 | 2 wks | 4 wks | 8 wks | T = 0 | 2 wks | 4 wks | 8 wks |
| AD | Dextromethor-phan | 25/60 40/75 50 | 0.21 | | 0.25 0.18 | 0.20 0.72 | 101.4 | | 102.5 101.5 | 100.2 100.1 |
| BD | Dibasic calcium phosphate anhydrous | 25/60 40/75 50 | 0.38 | | 0.51 0.60 | 0.83 1.06 | 99.8 | | 94.2 94.9 | 88.9 99.9 |
| CD | Sodium carboxymethyl cellulose 7MF PH | 25/60 40/75 50 | 2.47 | | 2.26 1.21 | 3.76 4.83 | 100.4 | | 100.6 96.7 | 88.2 84.0 |
| DD | Hydroxypropyl cellulose JXF | 25/60 40/75 50 | 0.22 | | 0.21 0.20 | 0.17 0.18 | 102.7 | | 98.3 78.2 | 95.7 98.0 |
| ED | Hydroxyethyl-cellulose 250HHX | 25/60 40/75 50 | <LOQ | | <LOQ | 0.16 | 75.2 | | 86.7 66.0 | 68.8 101.7 |
| FD | Methyl-cellulose A4M | 25/60 40/75 50 | 0.29 | | 0.27 0.25 | 0.26 0.26 | 87.2 | | 94.1 93.3 | 70.7 60.1 |
| GD | Carbomer 971P | 25/60 40/75 50 | 0.25 | | 0.24 0.28 | 1.11 0.29 | 81.8 | | 101.7 64.7 | 79.4 42.9 |
| HD | Cysteine HCl | 25/60 40/75 50 | 0.25 | | 0.21 0.18 | 0.52 0.20 | 75.1 | | 92.7 102.1 | 80.1 60.6 |
| ID | Ascorbic Acid | 25/60 40/75 50 | 0.22 | | 0.21 0.19 | 1.18 0.64 | 99.6 | | 97.1 92.1 | 96.5 105.0 |
| JD | Croscarmellose sodium | 25/60 40/75 50 | 0.35 | | 0.30 0.30 | 1.20 0.87 | 73.6 | | 78.5 69.2 | 77.6 72.5 |
| KD | Sodium starch glycolate | 25/60 40/75 50 | 0.24 | | 0.24 0.23 | 1.11 0.63 | 104.2 | | 98.4 85.9 | 89.8 116.8 |

Blend Compatibility:

The excipient compatibility studies clearly indicated instability of bupropion hydrochloride in presence of excipients. The most stable mixtures were observed using a 1:1 molar ratio of bupropion:cysteine hydrochloride and a 1:1 molar ratio of bupropion:ascorbic acid.

A blend stability study was set-up to evaluate the compatibility of bupropion hydrochloride with cysteine hydrochloride in a 1:0.5 molar ratio and a 1:2 ratio in combination with other commonly used excipients. The polymers were restricted to Carbopol971P and Methocel A4M. Similarly, a study was set-up using a combination of bupropion hydrochloride and ascorbic acid. The details of this study and the sample ID #'s are listed in Xcelience protocol #P0328-001B. The composition of samples as well as the results of the blend compatibility study have been presented in Table 5.

ibility study as well as blend compatibility study, following conclusions were derived.

Bupropion hydrochloride in combination with dextromethorphan exhibited stability and thus, a combination product in form of a bilayer tablet was feasible Dextromethorphan posed no incompatibility issue with the excipients used in the study, except sodium carboxymethylcellulose To maintain the stability of bupropion hydrochloride in the formulation, cysteine hydrochloride will be used in 1:2 molar ratio.

Prototypes containing either methyl cellulose or Carbopol as release controlling polymer will be designed, due to the least incompatibility observed with these polymers.

TABLE 5

Blend compatibility study

| Sample ID | Sample | Time Point/ Cond | TOTAL RS | | | | ASSAY | | | |
|---|---|---|---|---|---|---|---|---|---|---|
| | | | T = 0 | 2 wks | 4 wks | 8 wks | T = 0 | 2 wks | 4 wks | 8 wks |
| Ai | Bup (1)/Cys HCl (0.5)/MC | 25/60 40/75 50 | ND | 1.1 | 1.8 | 1.34 | 80.4 | 80.2 | 97.1 | 108.3 |
| Aii | Bup (1)/Cys HCl (2)/MC | 25/60 40/75 50 | ND | 0.13 | 0.3 | 0.1 | 59.2 | 102.6 | 102.3 | 98.9 |
| Bi | Bup (1)/Asc Acid (0.5)/MC | 25/60 40/75 50 | <LOQ | 11.7 | 16.43 | NA | 66.5 | 60.1 | 82.86 | NA |
| Bii | Bup (1)/Asc Acid (2)/MC | 25/60 40/75 50 | ND | 8.4 | 21.64 | NA | 103.1 | 78.1 | 84.7 | NA |
| Ci | Bup (1)/Asc Acid (0.5)/HPC | 25/60 40/75 50 | ND | 14.7 | 33.00 | NA | 89.0 | 67.8 | 71.4 | NA |
| Cii | Bup (1)/Asc Acid (2)/HPC | 25/60 40/75 50 | ND | 24.9 | 34.6 | NA | 79.4 | 81.4 | 69.9 | NA |
| Di | Bup (1)/Asc Acid (0.5)/NaCMC | 25/60 40/75 50 | 0.20 | 17.9 | 49.1 | NA | 46.7 | 34.8 | 43.9 | NA |
| Dii | Bup (1)/Asc Acid (2)/NaCMC | 25/60 40/75 50 | 0.16 | 19.4 | 34.2 | NA | 45.1 | 42.0 | 53.8 | NA |
| Ei | Bup (1)/Cys HCl (0.5)/Carbopol 971P | 25/60 40/75 50 | <LOQ | 0.47 | 1.0 | 1.98 | 83.8 | 39.4 | 72.4 | 84.3 |
| Eii | Bup (1)/Cys HCl (2)/Carbopol 971P | 25/60 40/75 50 | ND | 0.12 | 0.10 | 0.28 | 86.5 | 55.2 | 87.3 | 93.3 |

Note:
Bup: Bupropion;
Cys HCl: Cysteine hydrochloride;
MC: Methyl cellulose;
Asc Acid: Ascorbic acid;
HPC: Hydroxypropyl cellulose;
NaCMC: Sodium carboxymethylcellulose;
NA: Not tested based on results of t = 2 weeks.

Excipient Compatibility Study Conclusion

The data clearly demonstrated the stability of bupropion in presence of cysteine was significantly better as compared to ascorbic acid, specifically when cysteine was used at twice the molar amount of bupropion hydrochloride. This data was used to initiate formulation development with bupropion hydrochloride and cysteine hydrochloride in a 1:2 molar ratio. Based on the results of the excipient compat- Formulation Development Formulation development was initiated for BUP105/DEX45 bilayer tablets.

The proposal was to develop the bilayer tablets and use the BUP105 portion to a weight proportional BUP150 tablet with a placebo second layer to match the appearance of both tablets.

In the bupropion hydrochloride layer, Cysteine hydrochloride was used as a stabilizing agent for bupropion hydrochloride, methyl cellulose or Carbopol was used as a release controlling polymer (and binder), microcrystalline cellulose was used as the filler, and magnesium stearate was used as the lubricant. In the dextromethorphan hydrobromide, microcrystalline cellulose was used as filler, croscarmellose sodium was used as the disintegrant, and magnesium stearate was used as the lubricant.

Cysteine hydrochloride was maintained at a 2:1 molar ratio with the API. Prototype 1 and 2 used Methocel A4M as the release controlling polymer at 75 mg/tablet and 39.97 mg/tablet. Prototype 3 and 4 were formulated using Carbopol 971P as the release controlling polymer.

The formulation for the bilayer tablet comprising bupropion hydrochloride, Cysteine hydrochloride monohydrate, and dextromethorphan hydrobromide, used prototypes 9 and 10 as shown in Table 6 below, wherein the molar ratio of the bupropion to the cysteine was 1:1.

TABLE 6

Formulation recipe - prototypes 9-10

| Material | Qty. (mg/tablet) | | | |
|---|---|---|---|---|
| Prototype # | 9 | | 10 | |
| Blend Batch # | N3123-42 | | N3123-43 | |
| Compression Batch # | N3123-46B | N3123-46A | N3123-47B | N3123-47A |
| Layer 1 | | | | |
| Intragranular | | | | |
| Bupropion HCl | 105 | 150.0 | 105 | 150.0 |
| Cysteine HCl, Monohydrate | 66.76 | 95.37 | 66.76 | 95.37 |
| Carbopol 971P | 50 | 71.43 | 40 | 57.14 |
| Microcrystalline Cellulose PH 101 | 109.5 | 156.43 | 119.52 | 170.74 |
| Extragranular | | | | |
| Microcrystalline Cellulose PH 102 | 59.76 | 85.37 | 59.76 | 85.37 |
| Colloidal Silicon dioxide (Cabosil M5P) | 4 | 5.71 | 4 | 5.71 |
| Magnesium Stearate | 5 | 7.14 | 5 | 7.14 |
| Total layer weight | 400 | 570 | 400 | 570 |
| Layer 2 (N3123-45) | | | | |
| Dextromethorphan HBr | 45 | NA | 45 | NA |
| Microcrystalline cellulose PH 102 | 114.37 | NA | 114.37 | NA |
| Croscarmellose sodium | 8.5 | NA | 8.5 | NA |
| Magnesium stearate | 2.13 | NA | 2.13 | NA |
| Total layer weight | 170 | NA | 170 | NA |
| Total bilayer core tablet weight | 570 | 570 | 570 | 570 |
| COATING | | | | |
| Coating Batch # | N/A[3] | N3123-49A | N3123-48B | N3123-48A |
| Opadry II[1] | 22.8 | 22.8 | 22.8 | 22.8 |
| Purified Water[2] | — | — | — | — |
| Total | 592.8 | 592.8 | 592.8 | 592.8 |

[1]Target weight gain during coating: 4%.
[2]Evaporated during coating/drying process.
[3]Coating was not performed on this batch.

CONCLUSIONS

Prototype 10 was chosen to be used for future clinical trial batches. The above data was used to support the GMP manufacturing of bupropion hydrochloride 150 mg tablets, and bupropion hydrochloride 105 mg/dextromethorphan hydrobromide 45 mg tablets. The coating evaluation study performed in Batch #N3123-49A (prototype 9) was used to support the coating process to minimize the tablet surface abrasion issue. The coated tablets from prototype 10 (N3123-48A and 48B) were placed on informal stability testing at accelerated conditions.

Unless otherwise indicated, all numbers expressing quantities of ingredients, properties such as amounts, percentage, and so forth used in the specification and embodiments are to be understood in all instances as indicating both the exact values as shown and as being modified by the term "about." Accordingly, unless indicated to the contrary, the numerical parameters set forth in the specification and attached embodiments are approximations that may vary depending upon the desired properties sought to be obtained. At the very least, and not as an attempt to limit the application of the doctrine of equivalents to the scope of the embodiments, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms "a," "an," "the" and similar referents used in the context of describing the embodiments (especially in the context of the following embodiments) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any embodiment. No language in the specification should be construed as indicating any non-claimed element essential to the practice of the embodiments.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended embodiments.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the embodiments include all modifications and equivalents of the subject matter recited in the embodiments as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the embodiments. Other modifications that may be employed are within the scope of the embodiments. Thus, by way of example, but not of limitation, alternative embodiments may be utilized in accordance with the teachings herein. Accordingly, the embodiments are not limited to embodiments precisely as shown and described.

The invention claimed is:

1. A method of treating depression in a human being in need thereof with a dosage form comprising dextromethorphan, bupropion and cysteine, comprising orally administering the dosage form comprising the dextromethorphan, the bupropion, and the cysteine, wherein the dosage form is a solid and comprises the dextromethorphan in the free base form or a salt form, about 100 mg to about 120 mg of the bupropion in the free base form or a salt form, and about 50 mg to about 100 mg of the cysteine in the neutral form or a salt form, wherein the dosage form has a molar ratio of the bupropion to the cysteine that is about 0.5:1 to about 1.1:1, wherein bupropion and dextromethorphan, are the only therapeutic active agents in the dosage form, wherein the dosage form is a bilayer dosage form, and wherein the bupropion and the cysteine are in a first layer and the dextromethorphan is in a second layer.

2. The method of claim 1, wherein the dosage form has a molar ratio of the bupropion to the cysteine that is about 0.7:1 to about 1.1:1.

3. The method of claim 1, wherein the molar ratio of the bupropion to the cysteine is about 1:1.

4. The method of claim 1, wherein the dosage form further comprises a sustained release polymer.

5. The method of claim 4, wherein the sustained release polymer is an acrylate polymer or copolymer, a methylcellulose, or a combination thereof.

6. The method of claim 1, wherein the dosage form is in the form of a capsule, a pill, or a tablet.

7. The method of claim 1, wherein the dosage form further comprises a filler.

8. The method of claim 7, wherein the filler is microcrystalline cellulose.

9. The method of claim 1, wherein the dosage form further comprises a lubricant.

10. The method of claim 9, wherein the lubricant is magnesium stearate.

11. The method of claim 1, wherein the cysteine is L-cysteine hydrochloride monohydrate.

12. The method of claim 1, wherein the dosage form comprises a molecular complex of bupropion and cysteine.

13. The method of claim 1, wherein the bupropion in the dosage form is more stable than bupropion alone.

14. The method of claim 12, wherein the bupropion in the dosage form is more stable than bupropion alone.

15. The method of claim 1, wherein the bupropion is bupropion hydrochloride.

16. The method of claim 15, wherein the cysteine is L-cysteine hydrochloride monohydrate.

17. The method of claim 16, wherein the molar ratio of the bupropion to the cysteine is about 1:1.

\* \* \* \* \*